(12) United States Patent
Mick et al.

(10) Patent No.: US 9,064,672 B2
(45) Date of Patent: Jun. 23, 2015

(54) SPECIMEN MOUNT FOR MICROSCOPY (75) Inventors: Stephen E. Mick, Apex, NC (US); John Damiano, Apex, NC (US); David P. Nackashi, Raleigh, NC (US)

(73) Assignee: PROTOCHIPS, INC., Raleigh, NC (US)

( * ) Notice: Subject to any disclaimer, the term of this patent is extended or adjusted under 35 U.S.C. 154(b) by 871 days.

(21) Appl. No.: 12/809,717

(22) PCT Filed: Dec. 22, 2008

(86) PCT No.: PCT/US2008/088052
§ 371 (c)(1),
(2), (4) Date: Oct. 20, 2010

(87) PCT Pub. No.: WO2009/086319
PCT Pub. Date: Jul. 9, 2009

(65) Prior Publication Data
US 2011/0032611 A1    Feb. 10, 2011

Related U.S. Application Data

(60) Provisional application No. 61/016,206, filed on Dec. 21, 2007.

(51) Int. Cl.
*G02B 21/00* (2006.01)
*H01J 37/20* (2006.01)
*G02B 21/30* (2006.01)
*H01J 37/28* (2006.01)

(52) U.S. Cl.
CPC ............... *H01J 37/20* (2013.01); *G02B 21/30* (2013.01); *H01J 37/28* (2013.01); *H01J 2237/2007* (2013.01); *H01J 2237/2008* (2013.01)

(58) Field of Classification Search
CPC ........ G02B 21/00; G02B 21/24; G02B 21/26; G02B 21/30
USPC .......................... 359/368, 395, 820
See application file for complete search history.

(56) References Cited

U.S. PATENT DOCUMENTS 2,481,554 A * 9/1949 Winstead ..................... 219/243
3,971,622 A 7/1976 Yoshinaga
(Continued)

FOREIGN PATENT DOCUMENTS

JP             6044936 A    2/1994
JP         2006052993 A    2/2006
(Continued)

OTHER PUBLICATIONS

Supplementary European Search Report; Jul. 31, 2012.
Japanese Office Action and English Translation, Sep. 10, 2013.

*Primary Examiner* — Thong Nguyen
(74) *Attorney, Agent, or Firm* — Tristan A. Fuierer; Moore & Van Allen, PLLC (57) ABSTRACT

Mounts, stages, and systems that allow for in situ manipulation, experimentation and analysis of specimens directly within an electron microscope. The mounts fixture and interface with a device, wherein the device corresponds to a structure that holds a specimen for microscopic imaging. The mounts are mateably and/or electrically compatible with a stage. Systems using the devices, mounts, and stages that can be used directly within the electron microscope are disclosed.

17 Claims, 8 Drawing Sheets

(56) References Cited

U.S. PATENT DOCUMENTS

| | | | | |
|---|---|---|---|---|
| 4,888,463 A | * | 12/1989 | Middlebrook | 219/201 |
| 5,124,645 A | | 6/1992 | Rhoden et al. | |
| 5,343,018 A | * | 8/1994 | Limbach | 219/200 |
| 5,552,321 A | * | 9/1996 | Focht | 435/286.1 |
| 5,821,545 A | | 10/1998 | Lindsay et al. | |
| 6,951,419 B2 | * | 10/2005 | Tsuchiya | 374/100 |
| 7,713,053 B2 | | 5/2010 | Mick et al. | |
| 2006/0025002 A1 | | 2/2006 | Zhang et al. | |
| 2007/0164218 A1 | | 7/2007 | Jesse et al. | |
| 2008/0067374 A1 | | 3/2008 | Ono et al. | |

FOREIGN PATENT DOCUMENTS

| | | | | |
|---|---|---|---|---|
| JP | 2007303946 A | | 11/2007 | |
| JP | 4267054 | * | 5/2009 | 359/395 |
| WO | 2006031104 A1 | | 3/2006 | |
| WO | 2008061224 A1 | | 5/2008 | |
| WO | 2008109406 A1 | | 9/2008 | |
| WO | 2008141147 A1 | | 11/2008 | |
| WO | 2009086319 A2 | | 7/2009 | |
| WO | 2009117412 A1 | | 9/2009 | |

* cited by examiner

SPECIMEN MOUNT FOR MICROSCOPY

CROSS-REFERENCE TO RELATED APPLICATIONS

This application is filed under the provisions of 35 U.S.C. §371 and claims the priority of International Patent Application No. PCT/US2008/088052 filed on 22 Dec. 2008 entitled "Specimen Mount for Microscopy" in the name of Stephen E. Mick, et al., which claims priority of U.S. Provisional Patent Application No. 61/016,206 filed on 21 Dec. 2007, both of which are hereby incorporated by reference herein in their entirety.

FIELD OF THE INVENTION

The invention generally relates to devices, mounts, stages, interfaces and systems for microscopy.

BACKGROUND OF THE INVENTION

Specimens are routinely analyzed by various types of electron microscopes such as SEM, STEM and TEM. Current electron microscope systems allow for imaging conditions such as magnification, focus, tilt and specimen location to be adjusted and microscope systems often have x-ray collection systems to collect x-ray data in real-time. However, few systems provide the ability to perform real-time specimen analysis with thermal, mechanical, chemical, optical and gaseous stimuli. When such analysis is needed, ex-situ reactors are often used, for example, an experiment may be performed under appropriate environmental conditions outside of the microscope followed by quenching or termination. A specimen is then prepared and analyzed in the microscope after the experiment of interest has taken place. Disadvantageously, the ex-situ method of experimentation followed by analysis is time-consuming and provides ambiguous results since it is often difficult to quench experiments at a known point. Accordingly, there is a need for devices, mounts, stages, interfaces and systems to be developed that allow for in situ manipulation, experimentation and analysis of specimens directly within an electron microscope.

SUMMARY OF THE INVENTION

The present invention generally relates to systems including mounts useful for mechanically receiving devices, wherein the mount may be mechanically received in a stage. The systems enable real-time in situ manipulation, experimentation and analysis of microscopy specimens.

In one aspect, a system for in situ manipulation, experimentation and analysis of at least one microscopy specimen directly within a microscope, said system comprising a mount and a stage, wherein the mount and the stage are electrically connectable, and wherein the stage is electrically connectable to the outside of the microscope via a conduit.

In another aspect, a method of manipulating, experimenting and analyzing a microscopy specimen in situ, said method comprising:
  placing a microscopy specimen on a device;
  fixturing the device in a mount;
  mateably interfacing the mount in a stage, wherein the mount and the stage are mechanically and electrically connectable;
  applying electricity to manipulate the specimen electrically, chemically and/or thermally; and
  detecting and analyzing the in situ changes.

Other aspects, features and advantages of the invention will be more fully apparent from the ensuing disclosure and appended claims.

BRIEF DESCRIPTION OF THE INVENTION AND PREFERRED EMBODIMENTS THEREOF

The present invention discloses novel mounts, stages, interfaces and systems to enable real-time manipulation, experimentation and analysis of specimens directly during microscopic imaging. One preferred embodiment of the invention provides novel mounts, stages, interfaces and systems to enable real-time manipulation, experimentation and analysis of specimens directly within the electron microscope. Devices with experimental regions comprised of thin membranes and integrated features that enable real-time analysis are generally discussed. Mounts that fixture and interface with these devices and that are compatible with stages of the present invention are also disclosed. Stages are disclosed that mate with and provide interfaces with the mount as well as provide electrical stimuli via connections to feed-throughs of the electron microscope. Interfaces are disclosed between devices and mounts and between mounts and stages described herein. Systems using the devices, mounts, stages and interfaces are disclosed.

As described herein, the devices, mounts, stages, interfaces and systems are generally applicable for microscopy. The following description is provided in reference to the features of the devices, mounts, stages and interfaces disclosed by the figures.

Figure 1A:
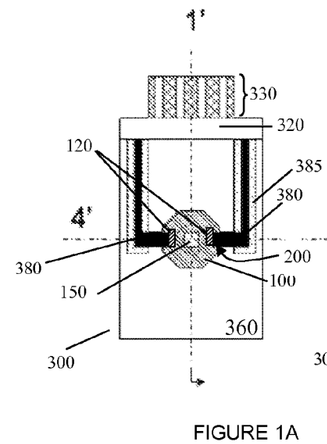
FIG. 1 illustrates four embodiments of the disclosed mount (300) with the fixtured device (100) from a top down view.

As used herein, a "device" corresponds to a structure that holds a specimen for microscopic imaging. A device provides electrical contacts and an experimental region. Devices may include one, more than one or even an array of experimental regions (see, e.g., FIG. 8) and may include integrated features such as electrodes (see, e.g., FIG. 1, (120), thermocouples, and/or calibration sites, as readily determined by one skilled in the art. One preferred embodiment includes devices made with MEMS technology and with thin membranes (continuous or perforated) for supporting a specimen in the experimental region. The devices provide electrical contacts or electrodes for connection to electrical leads on the mount. The devices also contain features to route electrical signals to the experimental region(s). The electrical signals on the devices may be routed on the device in any configuration including but not limited to pairs of signals routed to an experimental region or a row/column addressing scheme to access a greater number of experimental regions than the number of available signal leads. Preferred devices can be found in U.S. Provisional Patent Application 60/916,916, filed on May 9, 2007, and entitled "Microscopy Support Structures," and PCT Application No. PCT/US2008/141,147 filed on Nov. 20, 2008 and entitled "Microscopy Support Structures," which are both hereby incorporated by reference in their entirety, although it should be appreciated that the devices are not limited to those referenced therein. In a particularly preferred embodiment, the device comprises a membrane comprising at least one membrane region and at least one conductive element in contact with the membrane forming a heatable region of the membrane.

As used herein, a "mount" corresponds to a structure that fixtures a device and mates to a stage. Mounts interface to the device and the stage and maintain electrical connections. Referring to the embodiments of FIG. 1, the mount (300) is generally comprised of an offset (310), a standoff (320), a body (360), an electrical connector, e.g., a plug (330), a mechanical connector (350), a contact (200) and a void (340). The offset of the mount provides a region on the mount where devices are fixtured. The offset may protrude from (e.g., FIG. 1C and 1D), be flush with (e.g., FIG. 1A) or be recessed from (e.g., FIG. 1B) the top surface of the mount (361). The mount provides a plug (330) that may have electrical (332) connections that will mate with a receptacle on the stage. The standoff of the mount (320) extends from the side of the body of the mount (360) and serves multiple purposes. Firstly, it is the structure of the mount that protects the electrical (332) connections (338) of the plug (330) as they transition into the body of the mount. Also, the standoff provides a means to provide a gap between the stage receptacle and prior art mounts that do not have plugs built into them. It should be appreciated that although preferred, the standoff is not required as will be discussed hereinbelow.

The mount provides a void region (340) that allows electrons or other signals to pass through the mount to a signal detector that is situated below the device, mount, and stage. Alternatively, where the signal detector is situated above the device, mount and stage, the mount may provide voids below the experimental region(s) of the device(s) to confine transmitted electrons so that only electrons reflected from the specimen and device are detected.

The mount described herein is designed to fixture one or more devices and provides electrical contact to the device(s). Electrical wires or signal leads (380) are integrated into the mount and either coated in insulation or embedded in an insulating material 385) of the mount. One or more devices (100) may be placed on the offset region of the mount (310). The devices may be secured by providing two or more contacts (200) that clamp or screw the device(s) into place. Alternatively, the contacts may be spring loaded so that spring tension of the contacts on the device(s) holds the device(s) firmly in place on the offset region. The contacts are designed to provide electrical connection from the signal leads (380) to electrodes on the device (120). It should be appreciated that alternative securing means are contemplated when the contacts are not able to secure the device to the mount as readily determinable by one skilled in the art.

For example, FIG. 1 illustrates four embodiments of a mount (300) from a top down view. Each mount is shown with a single device (100) with an experimental region (150) fixtured upon the mount. Each mount may include two signal leads (380) embedded in the body (360) of the mount for making electrical connections from the mount to the device. Insulation (385) is shown around the signal leads (380). Each mount also shows a standoff (320) and an electrical connector, e.g., a plug (330) for mating into a receptacle on a stage. Each mount further shows an electrical contact (200) being made from each of the signal leads (380) to electrodes (120) on the device (100) that are then routed to the experimental region (150) of the device.

Figures 1B, 1C:
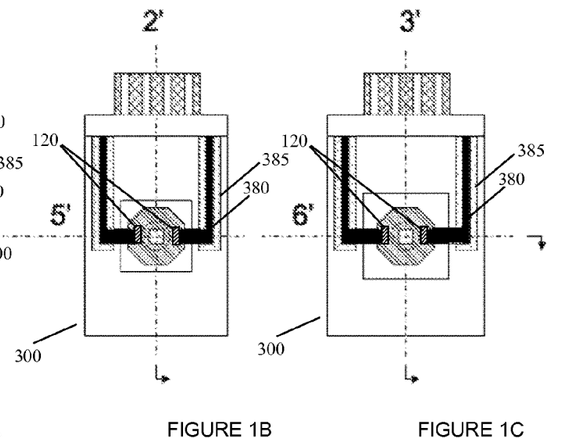
Figure 1D:
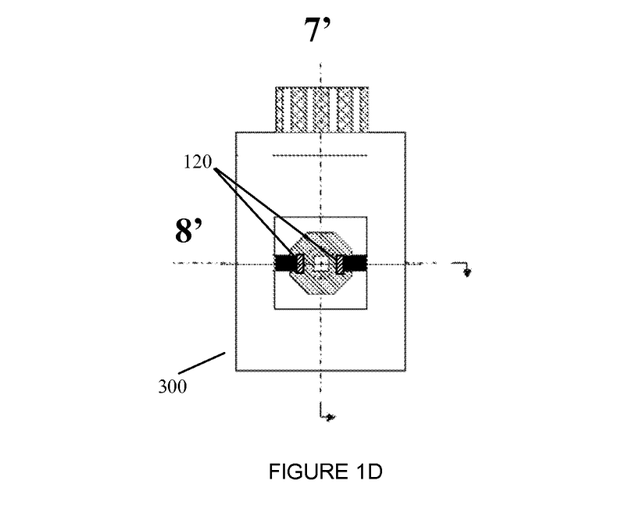
Figure 2:
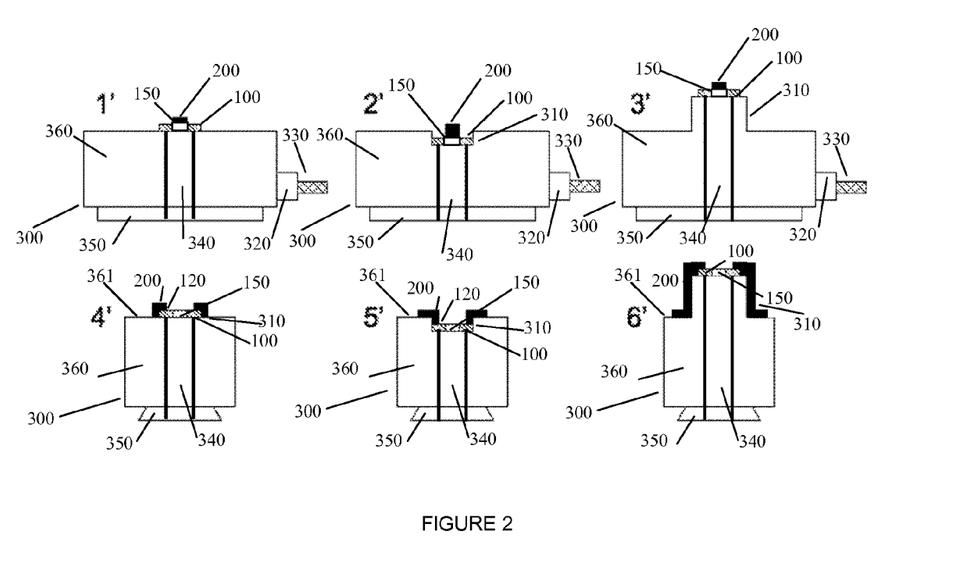
FIG. 2 illustrates side and front views of the mount (300) with the device (100) along the bisect lines 1', 2', 3', 4', 5', 6', 7', and 8' of FIGS. 1A-1D.

FIG. 2 illustrates side and front views of the mount (300) with the device (100) along the bisect lines 1', 2', 3', 4', 5', 6', 7', and 8' of FIGS. 1A-1D. In these views, the mount is shown to comprise the offset (310), standoff (320), an electrical connector, e.g., a plug (330), void (340), mateable connector (350), and body (360). The mount along bisect lines 1' and 4' includes an offset (310) that is flush with the top surface of the mount (361). The mount along bisect lines 2' and 5' includes the mount with an offset (310) that is recessed below the top surface of the mount (361). The mount along bisect line 3' and 6' and 7' and 8' includes the mount with an offset (310) that protrudes from the top surface of the mount (361). In FIG. 1C, the signal leads (380) are exposed while in FIG. 1D, the signal leads are embedded in the mount. With regards to FIG. 1D, the path the signal leads take should not be limited to that illustrated in the figure (the dotted line). A mateable connector (350), e.g., a dovetail, is shown at the bottom of each mount and is used to make physical and optionally electrical contact with a stage. Each mount has a void (340) in the region beneath the experimental region (150) of the device (100) to allow electrons to pass completely through the mount. Each mount further shows an electrical contact (200) that in the top view of FIG. 1 is seen to span from each of the signal leads (380) to electrodes (120) on the device (100). It should be appreciated that the matable connector illustrated herein corresponds to a dovetail but is not limited thereto.

As used herein, a "stage" corresponds to a structure within an electron microscope that passes electrical connections from a connector to the mount and optionally matably receives the mount. Stages may provide translation along three orthogonal axes as well as tilt and rotation. The mount (300) and the stage (400) may have mechanical and electrical interfaces. The mechanical interface between the stage (400) and mount (300) may be provided by a dovetail connection where the stage and mount have compatible parts of a dovetail joint. It should be appreciated that the matable connector illustrated herein corresponds to a dovetail but is not limited thereto. Electrical interfaces between the stage and mount may be provided by a plug mechanism (330) where the plug has embedded wires (332) for electrical connections and insulation (335) to separate adjacent wires. The mount and stage may also have contacts embedded in the mechanical connection, e.g., dovetail joint (see, e.g., FIG. 6 (370)), to make electrical connection between the stage and mount.

Figure 3A:
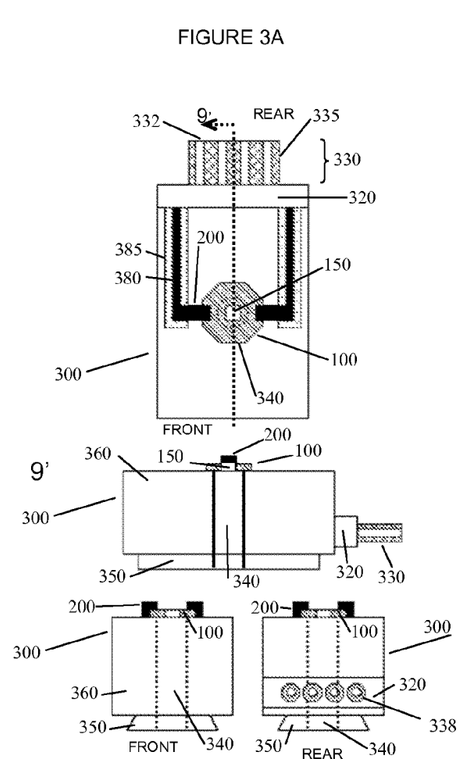
FIG. 3 illustrates a top view, bisect lines 9' and 10', and the front and rear views of a device (100), mount (300) and stage (400).
Figure 3B:
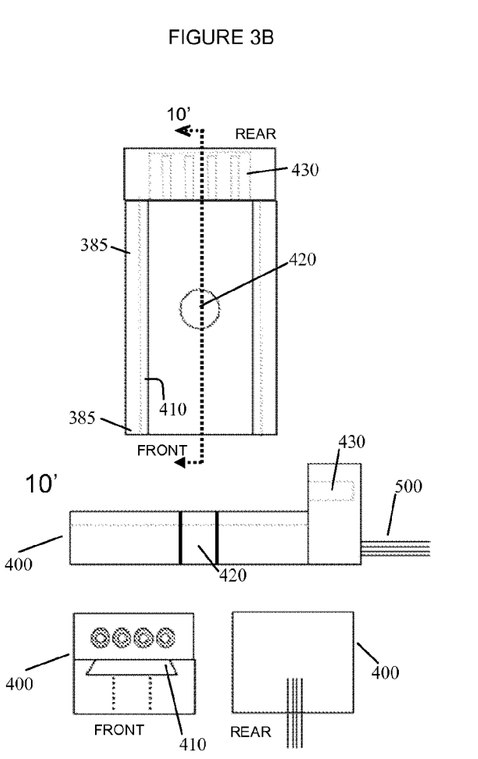

For example, FIG. 3 illustrates a top view, bisect lines 9' and 10', and the front and rear views of a device (100), mount (300) and stage (400). In this view the mount (300) comprises a standoff (320), an electrical connector, e.g., a plug (330), void (340), mateable connector (350), and body (360) and the stage (400) comprises a groove (410), stage void (420) and receptacle (430). As illustrated, the mount has a male plug-type (330) connector designed to connect to a female receptacle (430) of the stage when the mount and stage are mateably connected, e.g., with the dovetail joint. It should be appreciated that the male plug may be alternatively on the stage and the female receptacle on the mount. The stage is shown with a stage void (420) that when mated to the mount (300) is aligned to the void on the mount (340) and provides a continuous void through the mount and the stage for electrons to pass through. The mount void and the stage void are aligned beneath the experimental region (150) of the fixtured device (100). The mount shows two signal leads (380) embedded in the body (360) of the mount for making electrical connections through a contact (200) from the mount to the device. Insulation is shown around the signal leads (380). The plug (330) of the mount shows embedded plug wires (332) surrounded by insulation (335) although insulation is not required. The stage is shown to mate to a connector (500).

Figure 4:
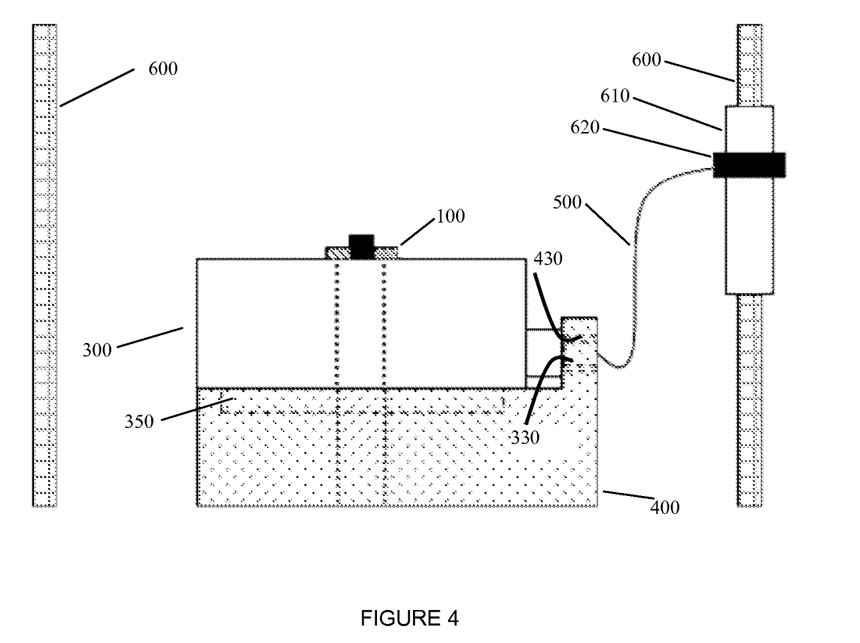
FIG. 4 illustrates a side view of a device (100) fixtured to a mount (300) and the combination of device and mount mated to a stage (400).

FIG. 4 shows a side view of a device (100) fixtured to a mount (300) and the combination of device and mount mated to a stage (400). The mateable connector of the mount (350) makes mechanical connection to the stage. A plug of the mount (330) is fitted into a receptacle of the stage (430) to enable electrical connections. The stage includes the plug/receptacle connections via a connector or conduit (500) that attaches to a port (620) in a feed-through (610) on the exterior wall (600) of an electron microscope. The connector or conduit (500) may be flexible to allow the stage to move within the chamber of the electron microscope. Alternatively, the connector may be rigid. The stage allows horizontal and vertical translation along three orthogonal axes while maintaining electrical connections to a mount. The stage further allows rotation and tilt while preserving electrical connections to the mount. The stage of the present invention is designed to be adapted to the stage of the electron microscope based upon the specific geometry of the stage of the electron microscope.

Figure 5A:
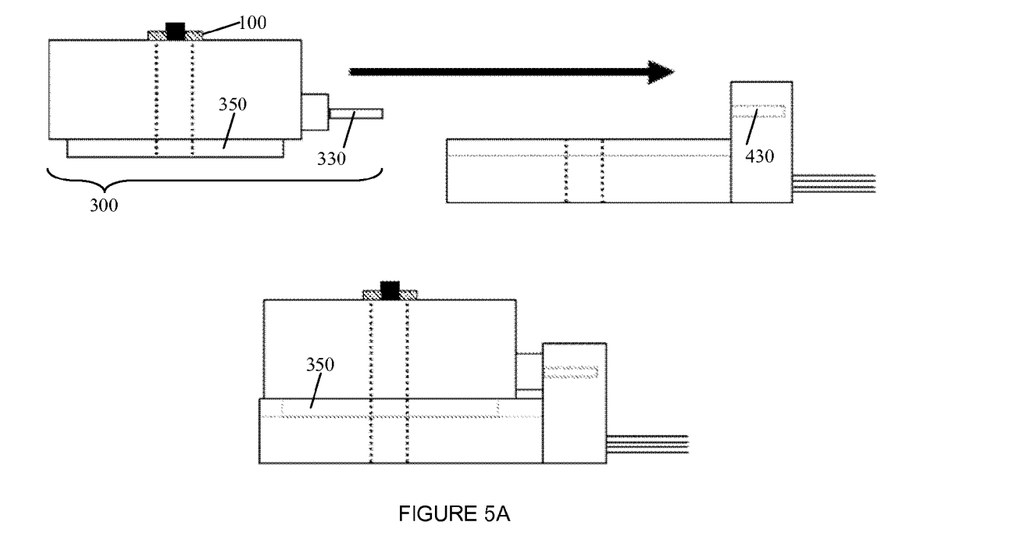
FIG. 5 illustrates two embodiments described herein including a mount (300) with a fixtured device (100) being mated to a stage (400) with dovetail (350) and plug-type (330) connections.
Figure 5B:
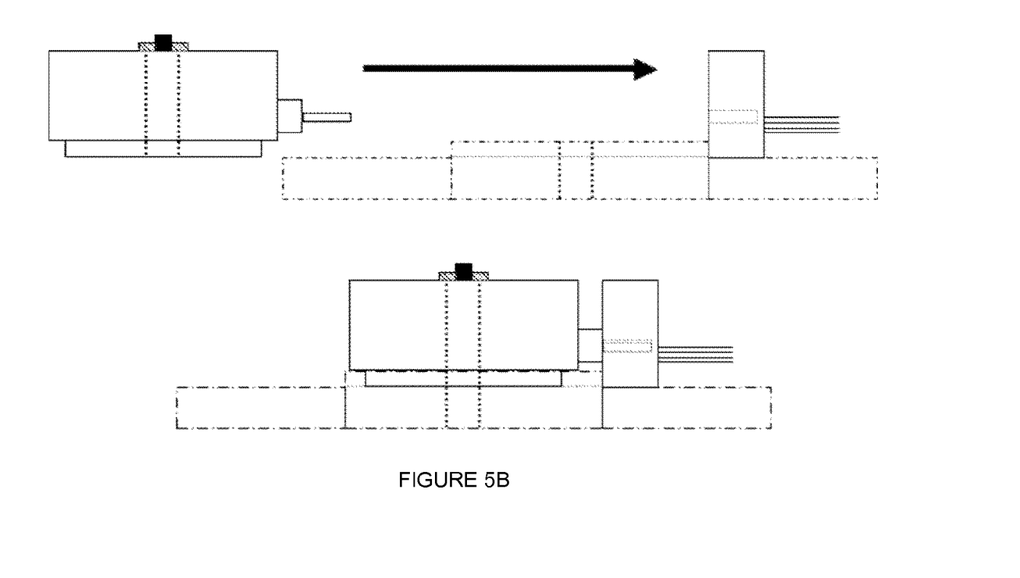

In one embodiment, the stage includes the electrical connections and the mechanical interface for matably engaging with the mount (see, e.g., FIG. 5A). In another embodiment, the stage includes just the electrical connections and instead utilizes mechanical interfaces already present in the microscope (see, e.g., FIG. 5B wherein the dotted lines represent an existing mechanical interface of a microscope).

Figure 6A:
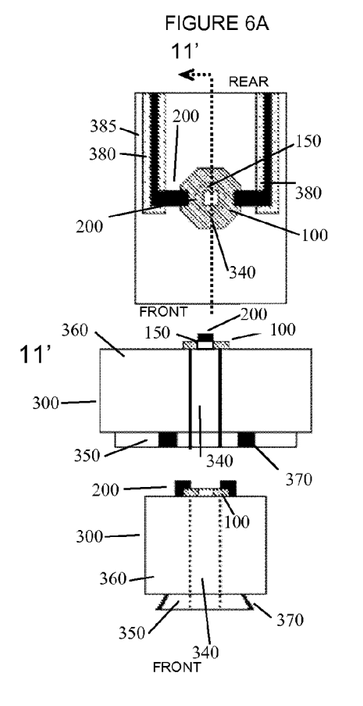
FIG. 6 illustrates a top view, bisect lines 11' and 12', and front and/or rear views of device (100), mount (300) and stage (400) showing a mateable (350) connection between the mount and stage with electrical connections integrated in the mateable connector, e.g., dovetail joint.
Figure 6B:
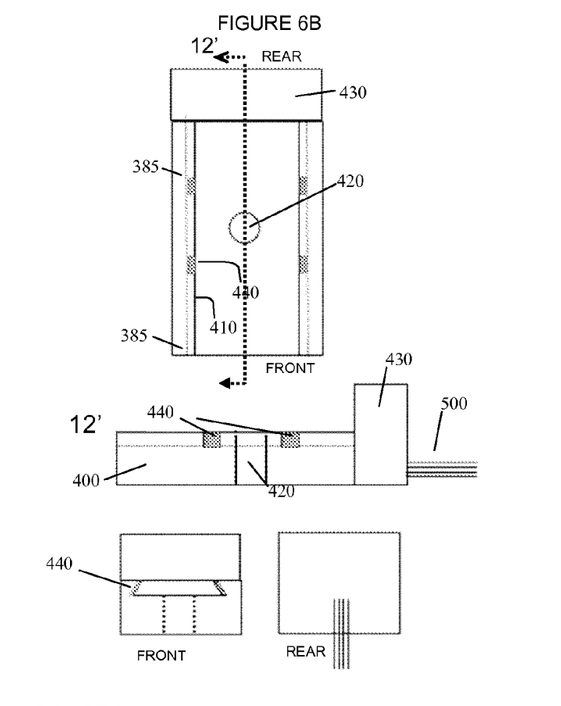
Figure 7:
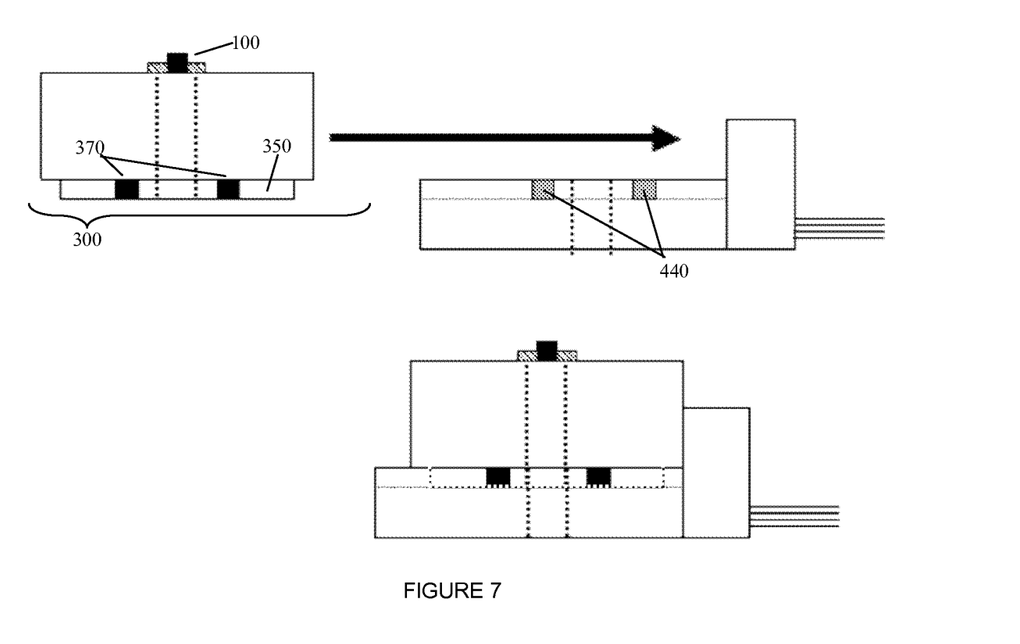
FIG. 7 illustrates a mount (300) with a fixtured device (100) being mated to a stage with mateable (350) connections, e.g., a dovetail, and with embedded mount contacts (370) aligned with and in contact with embedded stage contacts (440) in the mateable connector joint.

In another embodiment, the mount does not include the standoff (320) or the plug (330), but instead includes electrical connections integrated in the mateable connector, e.g., the dovetail joint. For example, FIG. 6 shows top, side and rear view of device (100), mount (300) and stage (400) showing the mateable (350) connection between the mount and stage with electrical connections integrated in the mateable connector, e.g., dovetail joint. The embedded mount contacts (370) and the embedded stage contacts (440) create a continuous electrical path from the stage to the mount when the mount is mated to the stage via the mateable connection. The stage comprises a groove (410), stage void (420) and receptacle (430). The mount connector (350) mates with the stage groove (410). The stage is shown with a stage void (420) that when mated to the mount (300) is aligned to the void on the mount (340) and provides a continuous void through the mount and the stage for electrons to pass through. The mount void and the stage void are aligned beneath the experimental region (150) of the fixtured device (100). The mount shows two signal leads (380) embedded in the body (360) of the mount for making electrical connections through a contact (200) from the mount to the device. Insulation is shown around the signal leads (380). The stage is shown to mate to a connector (500). It should be appreciated that although the signal leads (380) are illustrated as being viewable in the top view of FIG. 6A, the embodiment is not limited as such and may include signal leads that are embedded within the mount and connect the electrical contact (200) to the embedded mount contacts (370).

Regardless of the embodiment, the mount may be loaded in an electron microscope and be mated to the stage by hand or, for electron microscopes that provide a vacuum interlock, the mount may be loaded into the interlock and then mated to the stage with a transfer rod mechanism.

Figure 8A:
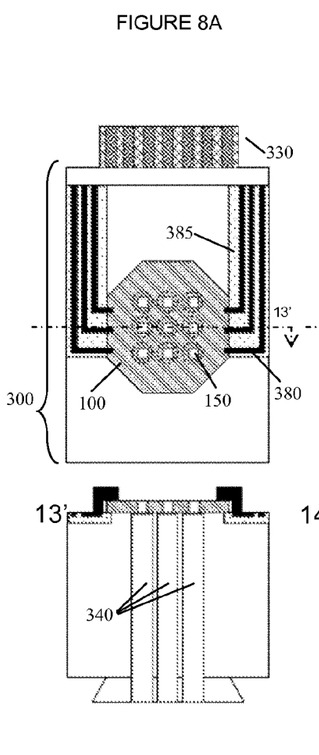
FIG. 8 illustrates examples of devices (100) with multiple experimental regions (150) fixtured to mounts (300) that can support numerous electrical connections (380).
Figure 8B:
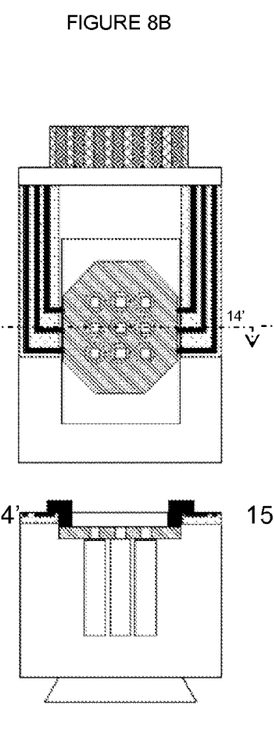
Figure 8C:
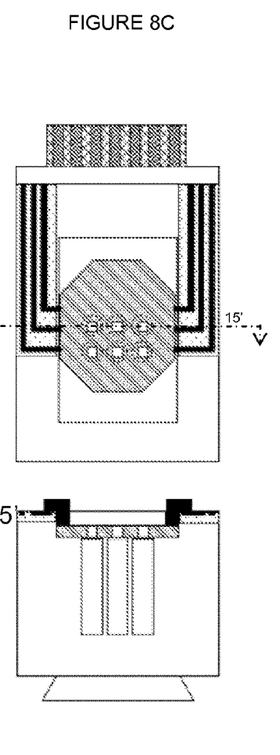

FIG. 8 shows examples of devices (100) with multiple experimental regions (150) fixtured to mounts (300) that can support numerous electrical connections (380). Insulation is shown around the signal leads (380). The voids (340) of all of the mounts in the figure are situated in the region beneath the experimental regions (150) of the device (100). The voids (340) of the mount in FIG. 8A extend completely through the mount as described hereinabove. The voids (340) of the mounts in FIGS. 8B and 8C extend only part way into the mount and provide a trap to electrons rather than a path through the mount which allows for signal detection from above the device, mount and stage. It should be appreciated that the number of plugs and/or signal leads illustrated is not intended to limit the system in any way.

A system as described herein makes use of one or more of the device, mount and/or stage for in situ manipulation, experimentation and analysis of specimens directly within an electron microscope. One non-limiting use of a system described herein is to use a device that transduces electrical signals to heat where the device is fixtured to a mount and electrical contact is made from the devices to the mount. The mount is further mated to a stage with electrical connections. For imaging and analysis that uses a signal detector that is situated below the device, mount, and stage, the mount and stage would preferably have a region directly underneath the experimental region of the devices that allows electrons or other signal to pass through the mount and stage to the detector. Electrical signals can then be applied from the outside of the microscope to the device and thermal experiments can be conducted directly within the electron microscope and in situ imaging can be done with the STEM mode of an electron microscope. For imaging and analysis that uses a signal detector that is situated above the device, mount, and stage, the mount and stage would preferably have a region directly underneath the experimental region of the devices that traps transmitted electrons or other signal and thus greatly limits the signal reaching the detector to that which originates from the specimen and experimental region of the device. Electrical signals can then be applied from the outside of the microscope to the device and thermal experiments can be conducted directly within the electron microscope and in situ imaging can be done with the SEM mode of an electron microscope.

A system as described herein may be used to conduct single experiments or multiple experiments. Devices that support multiple experiments may be used with a system to conduct experiments sequentially, simultaneously with other experiments, or as any combination of simultaneous and sequential experiments. One non-limiting use of a system comprised of a device with an array of experimental sites for thermal testing, a mount, a stage, and electrical connections would be to conduct experiments that vary the temperature and time of thermal exposure across the array of experimental sites. Another non-limiting use of a system would be to investigate electron beam induced effects. In still another embodiment, the system is operated in a vacuum or alternatively in a microscope adapted to operate in a gaseous environment.

Accordingly, while the invention has been described herein in reference to specific aspects, features and illustrative embodiments of the invention, it will be appreciated that the utility of the invention is not thus limited, but rather extends to and encompasses numerous other aspects, features, and embodiments. Accordingly, the claims hereafter set forth are intended to be correspondingly broadly construed, as including all such aspects, features, and embodiments, within their spirit and scope.

We claim:

1. A system for in situ manipulation, experimentation and analysis of at least one microscopy specimen directly within a microscope, said system comprising a mount that interfaces with a stage,
   wherein the mount comprises two or more contacts that fixture a device to the mount, wherein the device is useful for supporting a specimen,
   wherein signal leads are embedded in, and electrically insulated from, the mount for making electrical connections from the mount to the device,
   wherein the stage comprises a receptacle that is electrically connectable to the mount, and
   wherein the receptacle is electrically connectable to an external wall of the microscope.

2. The system of claim 1, wherein the device comprises:
   (a) a membrane comprising at least one membrane region; and
   (b) at least one conductive element in contact with the membrane.

3. The system of claim 1, wherein the mount comprises a top and a bottom and at least one of a mateable mount connector and an electrical mount connector.

4. The system of claim 3, wherein the mateable mount connector is positioned on the bottom of the mount and makes physical and electrical contact with the stage.

5. The system of claim 1, further comprising a mount void, wherein the mount void permits electrons or other signals to pass through the mount and the device to a detector.

6. The system of claim 1, wherein the stage comprises a top and a bottom and a mateable stage connector.

7. The system of claim 6, wherein the mateable stage connector is positioned on the top of the stage for mechanical interfacing with the mount.

8. The system of claim 6, wherein the stage further comprises a stage void that permits electrons or other signals to pass through the stage.

9. The system of claim 6, wherein the mateable stage connector includes at least one electrical stage connector thereon.

10. The system of claim 6, wherein the mateable stage connector is positioned on the top of the stage and makes physical and electrical contact with the mount.

11. The system of claim 1, wherein the stage is fixable to a microscope stage.

12. The system of claim 1, wherein the system provides electrical and/or thermal stimuli to the specimen for in situ experiments.

13. The system of claim 1 for single in situ experiments, for multiple, sequential in situ experiments, or for multiple, simultaneous in situ experiments.

14. The system of claim 1, wherein a conduit connects the receptacle to an exterior wall of the microscope to enable electrical connections, wherein the conduit comprises an electrical wire extending therethrough.

15. A method of manipulating, experimenting and analyzing a microscopy specimen in situ, said method comprising:
   placing a microscopy specimen on a device;
   fixturing the device in a system of claim 1;
   applying electricity to manipulate the specimen electrically, chemically and/or thermally; and
   detecting and analyzing the in situ changes.

16. The system of claim 1, wherein the two or more contacts provide an electrical connection from the signal leads on the mount to an electrode on the device.

17. The system of claim 1, wherein the two or more contacts are spring loaded so that spring tension fixtures the device to the mount.

* * * * *